United States Patent [19]
Raiken

[11] Patent Number: 5,653,719
[45] Date of Patent: Aug. 5, 1997

[54] KNOT PUSHING INSTRUMENT FOR ENDOSCOPIC SURGERY

[76] Inventor: Steve Raiken, 11121 Barman Ave., Culver City, Calif. 90230

[21] Appl. No.: 533,542

[22] Filed: Sep. 25, 1995

[51] Int. Cl.$^6$ ............................................. A61B 17/04
[52] U.S. Cl. ............................................. 606/148
[58] Field of Search ........................ 606/148, 139, 606/103; 289/17

[56] References Cited

U.S. PATENT DOCUMENTS

| | | | |
|---|---|---|---|
| 3,131,957 | 5/1964 | Musto | 289/17 |
| 5,324,298 | 6/1994 | Phillips et al. | 606/148 |
| 5,397,326 | 3/1995 | Mangum | 606/148 |

*Primary Examiner*—Michael Buiz
*Assistant Examiner*—Tina T. D. Pham
*Attorney, Agent, or Firm*—Frederick Gotha

[57] ABSTRACT

A knot-pushing instrument consisting of an elongated member that has an axis of elongation and an axially extending cavity therein where the cavity is bounded at the distal end of the elongated member by the proximate face of a laterally extending distal wall. The distal wall has a transverse slit which extends through the wall and communicates with the cavity. A first axially extending slot communicates with both the cavity and the transverse slit and is so dimensioned and proportioned to permit a strand of suture to pass laterally through the first axially extending slot and into the cavity. The transverse slit is so dimensioned and proportioned to permit the strand of suture to advance axially through the transverse slit when a slip-type knot is pushed by the distal wall along the strand of suture. An open holding region which is proximately and axially removed from the distal end of the elongated member is positioned a fixed distance circumferentially from the first axially extending slot where the open holding region communicates with the cavity and the first axially extending slot. The open holding region is so configured and dimensioned to permit the strand of suture to be captively restrained laterally within the region while the strand of suture advances axially through the transverse slit.

14 Claims, 2 Drawing Sheets

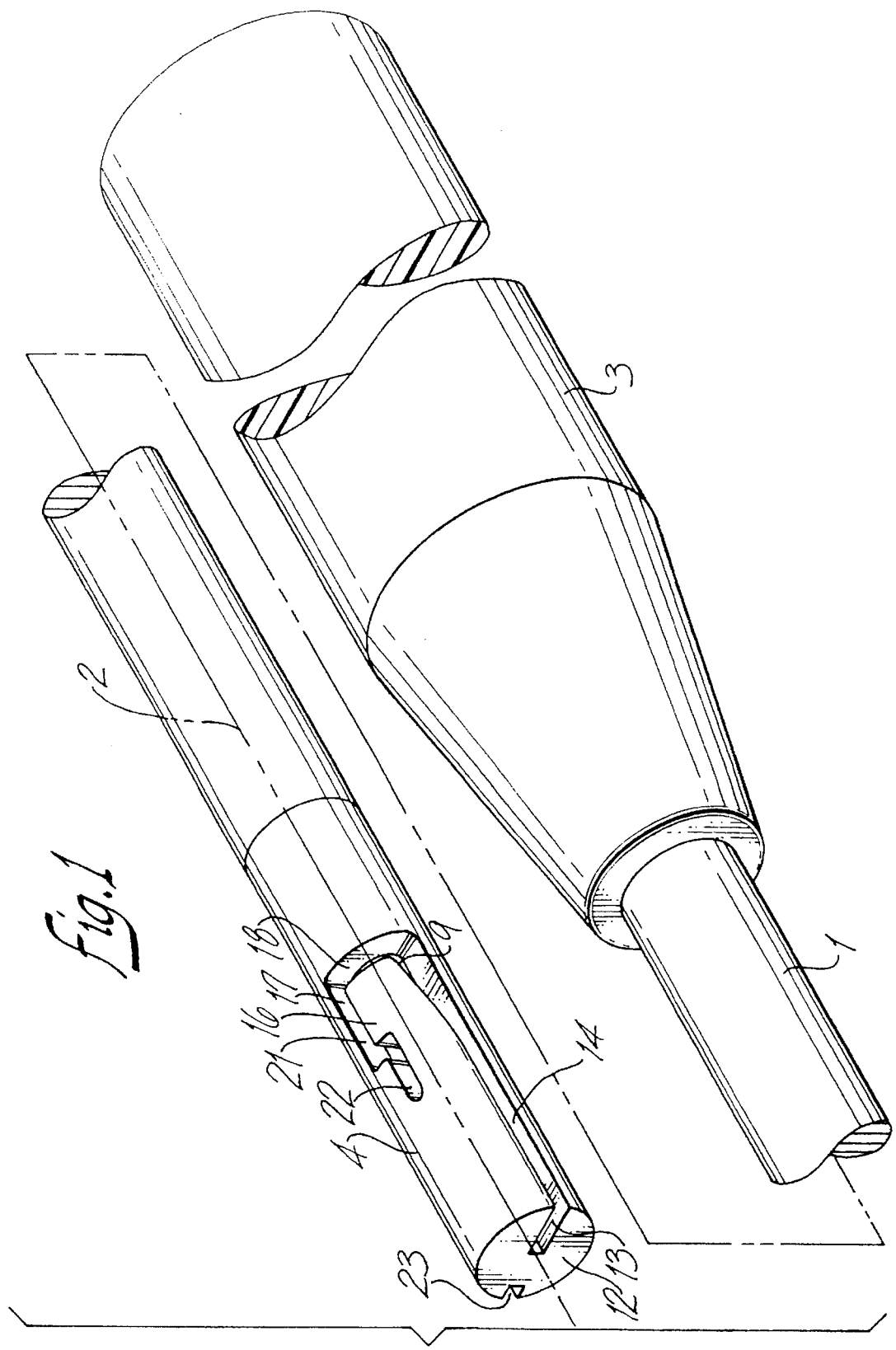

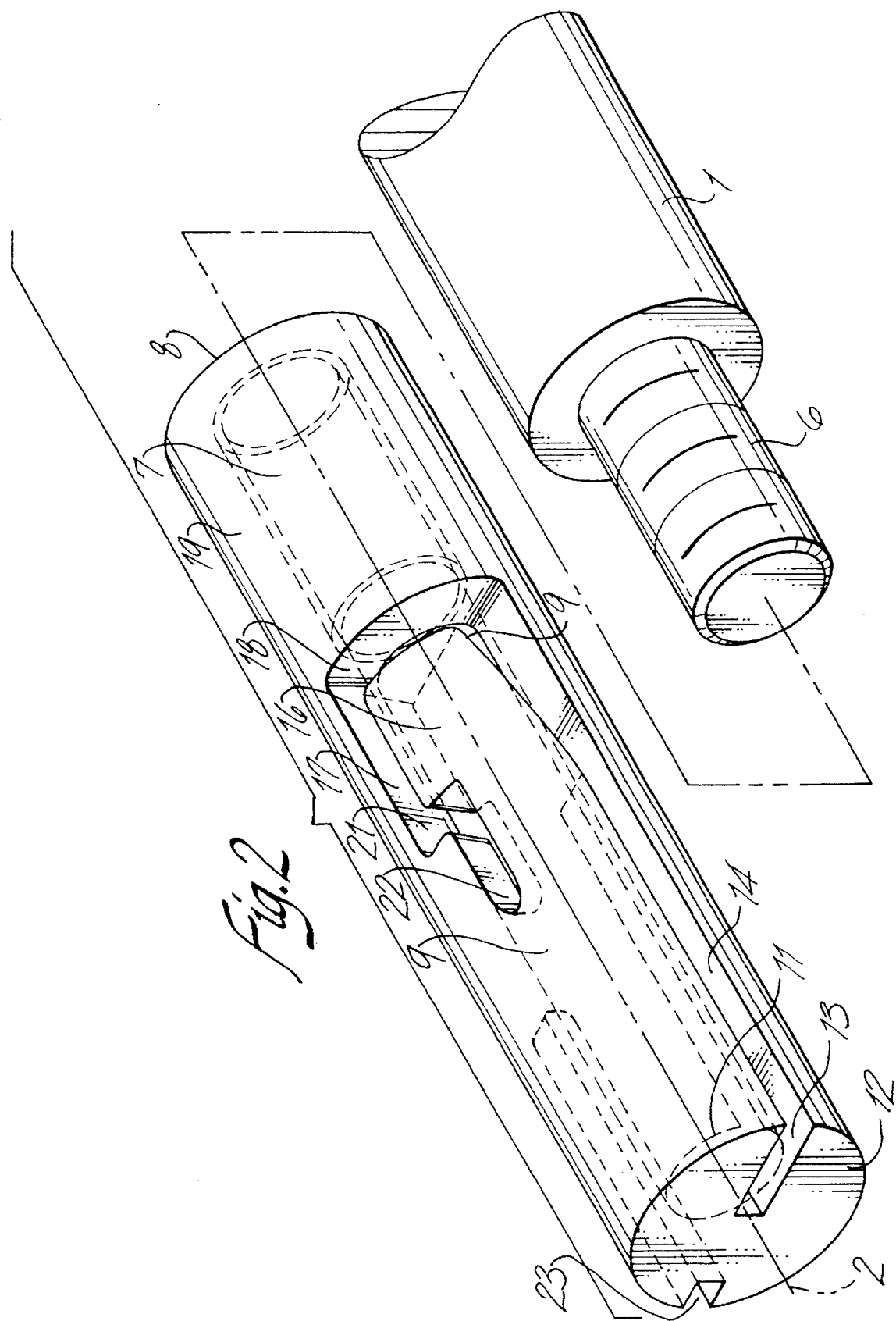

KNOT PUSHING INSTRUMENT FOR ENDOSCOPIC SURGERY

FIELD OF THE INVENTION

This invention relates to a surgical knot pushing instrument for use in the formation of a suture or ligature during endoscopic surgery.

BACKGROUND OF THE INVENTION

In recent years the increase demand by patients for minimal invasive surgery has required surgeons to perform intricate suturing and ligation procedures involving extra corporeal formation of slip-type knots on a suture strand and thereafter pushing the knot along the strand into the operative region.

Pushing a knot through a cannula to form a ligature or suture is well known in the prior art. In U.S. Pat. No. 5,324,298, a knot pushing instrument is described where the instrument utilizes a locking sleeve which is rotated relative to an elongated member in order to captively retain the strand of suture in a slot; thus, when a knot was pushed through a cannula the suture strand was permitted to advance axially through the slot while being captively held within the slot by the locking sleeve. One of the disadvantages in using this type of knot pushing instrument was that the surgeon was required to physically rotate the sleeve while holding that portion of the strand of suture which was to be locked into the slot. During surgical procedures, it is desirable to reduce the manipulations of a surgical instrument by the surgeon and thus reduce the time during which the patient is under anesthesia. Another disadvantage is the expense to manufacture an instrument which consists of two separate parts which must be assembled so as to permit relative rotation between the parts.

Another patent, U.S. Pat. No. 5,269,791, illustrates a knot pushing instrument of the prior art where a conical tapered coil was used at the distal end of the knot pushing instrument. The coil of that invention required the suture strand to be wound between the turns of the coil and the knot thereafter pushed into the operative region by the distal tip of the tapered coil. In order to push a knot with this instrument the surgeon was required to hold the suture strand, the instrument, and then wind the strand around the conical coil. Again, the manipulations required by the surgeon in order to captively retain the strand above the slip-type knot increased the time of the surgery and therefore the length of time under which the patient was kept under anesthesia.

It would therefore be advantageous to provide an inexpensive knot pushing instrument for use in minimum invasive surgery that would permit the surgeon to easily ensnare a strand of suture, captively retain the strand in a slot, and thereafter push the knot into the operative region by axially advancing the suture through the slot.

SUMMARY OF THE INVENTION

There is, therefore, provided according to the present invention, an improved endoscopic knot pushing instrument for pushing a slip-type knot along a strand of suture to form a suture or ligature during a minimal invasive surgical procedure.

The present invention is directed to an improved endoscopic surgical instrument for pushing a slip-type knot formed on a strand of suture along that strand of suture to form a ligature or suture during minimal invasive surgery.

The knot pushing instrument consists of an elongated member having a proximate and distal end and an axis of elongation. A cavity extends at least in part through the elongated member where the cavity is distally bounded by a distal wall that extends laterally from the axis of elongation and forms the distal end of the elongated member. The distal wall has a transverse slit which extends through the wall and communicates with the cavity; the slit having sufficient dimensions to permit the strand of suture to advance axially through the slit while the slip-type knot formed on that strand of suture is precluded from passing through the transverse slit. In order to engage and captively hold the suture strand, the elongated member has a first axially extending slot which communicates both with the cavity and the transverse slit where the slot is so dimensioned and proportioned to permit the strand of suture to freely pass laterally through the slot and into the cavity; the elongated member further has a holding region which is circumferentially displaced from the slot and located in fixed dimensional relationship with it. The holding region is an open region defined by a series of stepped and intersecting slots located proximally from the distal end of the elongated member and so configured and dimensioned that the strand of suture can be captively bounded within the region while the strand of suture advances axially through the transverse slit. Since the holding region is circumferentially displaced from the first axially extending slot and configured to hold the suture captively while at the same time allowing it to advance axially through the slit, the strand of suture above the slip-type knot after the knot is extracorporeally formed is easily snared into the first axially extending slot and then a portion of the strand circumferentially displaced into the holding region where it is captively held. In the preferred embodiment, the holding region has a second slot which has a stepped distal portion; the second slot is essentially parallel to the first axially extending slot. The step portion of the second slot retains the strand of suture a fixed circumferential distance from the first axially extending slot and thus permits the strand of suture to be captively contained within the cavity while the strand of suture axially advances through the transverse slit and holding region.

An instrument for easily snaring a strand of suture and thereafter pushing a slip-type knot formed on that strand of suture is therefore provided where the strand of suture above the slip-type knot is easily ensnared by a first axially extending slot and then laterally displaced through the first axial slot into a cavity. The cavity communicates with an open holding region defined by a stepped second slot circumferentially removed from the first slot. The second slot is so configured in a step configuration to permit the strand of suture to be captively removed from the first slot while the knot is being pushed.

BRIEF DESCRIPTION OF THE DRAWINGS

These and other features and advantages will become appreciated as the same become better understood with reference to the following specification, claims and drawings wherein:

FIG. 1 is a perspective view of the improved endoscopic knot pushing instrument of this invention illustrating the distal and proximate end segments of the instrument.

FIG. 2 is an enlarged perspective view of the distal portion of the endoscopic knot pushing instrument illustrated in FIG. 1.

DETAILED DESCRIPTION

The improved endoscopic knot pushing instrument of this invention is shown in perspective in FIG. 1. As can be seen in FIG. 1, the improved knot pushing instrument has an elongated member 1 having an axis of elongation 2, a handle portion 3 located at the proximate end of the elongated member and a tip portion 4 located at the distal end of elongated member 1. In forming a ligature endoscopically, the surgeon must introduce the suture material into the operative region by passing the suture material through a cannula member which communicates with the operative region. One method of introducing the suture material into the body cavity requires that a needle be attached to the suture material and after the needle is advanced through the cannula into the body cavity it is there grasped by the surgeon using a grasper tool to form a loop to snare tissue, tubes or vessels and the needle is then withdrawn by the surgeon through the cannula and a slip-type knot formed extracorporeally. The slip-type knot is then pushed along the strand of the suture by the surgeon utilizing a knot pushing instrument. Another method utilized by surgeons in forming a ligature is to introduce the free end of the suture through the cannula into the operative region where it is grasped by a grasper tool and then looped around a body structure. The free end is then withdrawn through the cannula, a slip-type knot formed extracorporeally, and the knot then pushed by the surgeon, utilizing a knot pushing instrument, back through the cannula until the knot tightens against the body structure thereby forming the ligature. The methods for forming a slip-type knot and pushing the knot into the operative region are not shown in the drawings; the methods are well known in the prior art.

The distal portion 4 of elongated member 1 is shown in an enlarged perspective view in FIG. 2. As can be seen in FIG. 2, tip portion 4 in a preferred embodiment is removably mountable to elongated member 1. However, tip portion 4 may in another embodiment be integrally part of the elongated member 1. By having the feature of removability, however, an appropriately dimensioned tip portion 4 may be fastened to the elongated member to accommodate a particular suture diameter.

Referring again to FIG. 2, it can be seen that elongated member 1 has an extension member 6 for insertion into a receiving chamber 7. In a preferred embodiment, receiving chamber 7 is threaded and located at the proximate end 8 of tip portion 4; fastening extension member 6 in the preferred embodiment is a threaded extension for insertion into threaded receiving chamber 7. Other fastening methods may also be used to removably mount tip portion 4 to elongated member 1 and to securely fasten the tip to the elongated member.

In the preferred embodiment of this invention, the tip portion 4 may be made of a plastic material and formed through plastic injection molding processes.

Tip portion 4 contains an axially extending cavity 9 therein which as can be seen in FIG. 2, is cylindrically shaped and communicates with the receiving chamber 7. Cavity 9 is bounded at its distal end 11 by distal wall 12. A transversely extending slit 13 extends through distal wall 12 and communicates with cavity 9; transversely extending slit 13 is of sufficient width to permit a strand of suture to advance axially through it and to prevent a slip-type knot formed on the strand of suture and bearing against distal wall 12 from passing through the transverse slit. A first axially extending slot 14 passes laterally in a radial direction through the surface of tip portion 4 and communicates with both cavity 9 and transverse slit 13. The communication of slot 14 with cavity 9 and transverse slit 13 permits the surgeon to easily ensnare a strand of suture into slot 14 and thereafter axially advance the suture through the slit 13 and cavity 9.

To captively hold a strand of suture while at the same time permitting it to be advanced axially through cavity 9, the tip portion 4 is designed to contain a holding region 16. As can be seen in FIG. 2, region 16 includes a second axially extending slot 17 and a circumferential slot 18 which communicates with both second axially extending slot 17 and first axially extending slot 14; as can be further seen in FIG. 2, second axially extending slot 17 and circumferential slot 18 extend through the surface 19 of the tip portion 4 and communicate with the internal cavity 9. Thus, a strand of suture may easily be ensnared along its length by moving the knot pusher instrument laterally against the strand of suture so as to pass the strand of suture through first axially extending slot and transversely extending slit 13. A portion of the strand of suture may then be passed through circumferential slot 18 and then looped into second axially extending slot 17.

In the preferred embodiment, to captively hold a strand of suture in the holding region 16 while at the same time permitting axial advance of the strand of suture through the cavity 9, a step slot 21, which is also an open slot through surface 19, is utilized. As can be seen in FIG. 2, step slot 21 also communicates with the cavity 9. Step slot 21 consists of a third axially extending slot 22 which is circumferentially displaced a fixed distance from second axially extending slot 17 and parallel thereto. Thus, the holding region 16 permits a strand of suture to axially advance through both the slit 13 and third slot 22. The lateral advance of the suture is restricted by step slot 21 and the suture captively retained within slot 22. The slip-type knot remains in bearing engagement with distal wall 12 as the strand of suture advances captively bounded within slot 22.

Under certain procedures, the surgeon may elect to tie a series of knots which requires him to hold the free end of the strand of suture; by holding the free end of the suture another knot may tied after the previous knot is tightened and the new knot again pushed by the knot pushing instrument into the operative region for tightening. A free end suture channel 23 is thus provided which permits the free end of the suture to be held in channel 23 while the other portion of the suture strand is axially advanced through transverse slit 13 and third slot 22 during the tightening procedure.

Thus, when the surgeon, during a minimal invasive procedure, desires to push a knot along the strand of suture into the operative region through a cannula, the strand of suture above the knot in accordance with this invention may be manipulated through first axially extending slot 14 into the cavity 9 and the more proximate portion of the strand then looped into the holding region 16 until the strand of suture is captively held in third axially extending slot 22; the free end of the strand of suture can then be securely held in channel 23 while the knot bears against distal wall 12 and the knot then advanced through the cannula by axial withdrawal of the other end of the suture through slit 13 and slot 22.

While I have shown and described an embodiment of the present improved knot pushing instrument, it is to be understood that the invention is subject to many modifications without departing from the scope and spirit of the claims as recited herein. This invention is not to be limited by the embodiment shown in the drawings and described in the description which is given by way of example and not of limitation.

What is claimed is:

1. An improved endoscopic knot pushing instrument for pushing a slip-type knot formed in a strand of suture along the strand of suture comprising:

a) an elongated member having a proximate end and a distal end, a peripheral surface, an axis of elongation and an axially extending cavity therein extending at least in part therethrough, said elongated member further having a distal wall comprising a distal face and a proximate face, said distal wall extending laterally from said axis of elongation at said distal end of said elongated member where said proximate face defines the distal boundary of said cavity, said distal wall further having a transverse slit extending axially therethrough and communicating with said cavity, said elongated member further having a first axially extending slot communicating with both said cavity and said transverse slit where said first axially extending slot is so dimensioned and proportioned to permit said strand of suture to pass laterally through said first axially extending slot and into said cavity, and where said transverse slit is so dimensioned and proportioned to permit said strand of suture to advance axially through said transverse slit when said slip-knot is pushed by said distal wall along said strand of suture, said elongated member having an open holding region proximately and axially removed from said distal end and positioned a fixed arcuate distance circumferentially from said first axially extending slot, said open holding region communicating with said cavity and said first axially extending slot, and where said open holding region is so configured and dimensioned to permit said strand of suture to be captively restrained laterally within said region while said strand of suture advances axially through said transverse slit.

2. The improved knot pushing instrument recited in claim 1 wherein said open holding region comprises a second axially extending slot circumferentially displaced from said first axially extending slot and in communication with said cavity where said second axially extending slot is so configured and dimensioned to permit said strand of suture to be captively retained therein while said strand of suture passes axially therethrough.

3. The improved knot pushing instrument recited in claim 2 wherein said holding region further comprises a circumferential slot interconnecting said first axially extending slot and said second axially extending slot and communicating with said cavity, said holding region further comprising a third axially extending slot located distally of said circumferential slot and arcuately removed a fixed distance circumferentially from said second axially extending slot, and a step slot circumferentially connecting said second axially extending slot and said third axially extending slot where said step slot communicates with said cavity.

4. The improved knot pushing instrument recited in claim 1 wherein said elongated member has an open suture channel in said peripheral surface laterally spaced from said first axially extending slot, said suture channel having an opening in said distal wall and extending in said peripheral surface.

5. An improved knot pushing instrument for pushing a slip-type knot formed in a strand of suture along the strand of suture comprising:

(a) an elongated member having a proximate end and a distal end and an axis of elongation;

(b) a tip portion having a peripheral surface removably mounted to said elongated member at said distal end, where said tip portion has an axially extending cavity extending at least in part therethrough and a distal wall comprising a distal face and a proximate face extending laterally where said proximate face defines the distal boundary of said cavity, said distal wall further having a transverse slit extending axially therethrough and communicating with said cavity, said tip portion further having a first axially extending slot communicating with said cavity and said transverse slit where said slot is so dimensioned and proportioned to permit said strand of suture to pass through said first axially extending slot and into said cavity, and where said transverse slit is so dimensioned and proportioned to permit said strand of suture to pass axially through said transverse slit when said slip-type knot is pushed by said distal wall along said strand of suture, said tip portion further having an open holding region distally and axially removed from said distal end and positioned arcuately a fixed distance circumferentially from said first axially extending slot and where said holding region is so configured and dimensioned to permit said strand of suture to be captively restrained from lateral movement within said holding region while said strand of suture advances axially through said holding region.

6. The improved knot pushing instrument recited in claim 5 wherein said open holding region comprises a second axially extending slot circumferentially displaced from said first axially extending slot and in communication with said cavity where said second axially extending slot is so configured and dimensioned to permit said strand of suture to be captively retained therein while said strand of suture passes axially therethrough.

7. The improved knot pushing instrument recited in claim 6 wherein said holding region further comprises a circumferential slot interconnecting said first axially extending slot and said second axially extending slot and communicating with said cavity, said holding region further comprising a third axially extending slot located distally of said circumferential slot and arcuately removed a fixed distance circumferentially from said second axially extending slot, and a step slot circumferentially connecting said second axially extending slot and said third axially extending slot where said step slot communicates with said cavity.

8. The improved knot pushing instrument recited in claim 5 wherein said tip portion has an open suture channel in said peripheral surface laterally spaced from said first axially extending slot, said suture channel having an opening in said distal wall and extending axially in said peripheral surface.

9. The improved knot pushing instrument recited in claim 6 wherein said tip portion has an open suture channel in said peripheral surface laterally spaced from said first axially extending slot, said suture channel having an opening in said distal wall and extending axially in said peripheral surface.

10. The improved knot pushing instrument recited in claim 7 wherein said tip portion has an open suture channel in said peripheral surface laterally spaced from said first axially extending slot, said suture channel having an opening in said distal wall and extending axially in said peripheral surface.

11. An improved knot pushing instrument for pushing a slip-type knot formed in a strand of suture along the strand of suture comprising:

a) an elongated member having a proximate end and a distal end, a peripheral surface, an axis of elongation and an axially extending cavity therein extending at least in part therethrough, said elongated member further having a distal wall comprising a distal face and a proximate face, said distal wall extending laterally from said axis of elongation at said distal end of said elongated member where said proximate face defines the distal boundary of said cavity, said distal wall further having a transverse slit extending axially therethrough and communicating with said cavity, said elongated member further having a first axially extending slot communicating with both said cavity and said transverse slit where said first axially extending slot is so dimensioned and proportioned to permit said strand of suture to pass laterally through said first axially extending slot and into said cavity, and where said transverse slit is so dimensioned and proportioned to permit said strand of suture to advance axially through said transverse slit when said slip-knot is pushed by said distal wall along said strand of suture, said elongated member having an open holding region proximately and axially removed from said distal end and positioned a fixed arcuate distance circumferentially from said first axially extending slot, said open holding region communicating with said cavity and said first axially extending slot, and where said open holding region is so configured and dimensioned to permit said strand of suture to be captively restrained laterally within said region while said strand of suture advances axially through said transverse slit, where said open holding region comprises a second axially extending slot circumferentially displaced from said first axially extending slot and in communication with said cavity where said second axially extending slot is so configured and dimensioned to permit said strand of suture to be captively retained therein while said strand of suture passes axially therethrough, and where said holding region further comprises a circumferential slot interconnecting said first axially extending slot and said second axially extending slot and communicating with said cavity, said holding region further comprising a third axially extending slot located distally of said circumferential slot and arcuately removed a fixed distance circumferentially from said second axially extending slot, and a step slot circumferentially connecting said second axially extending slot and said third axially extending slot where said step slot communicates with said cavity.

12. The improved knot pushing instrument recited in claim 11 wherein said elongated member has an open suture channel in said peripheral surface laterally spaced from said first axially extending slot, said suture channel having an opening in said distal wall and extending in said peripheral surface.

13. An improved knot pushing instrument for pushing a slip-type knot formed in a strand of suture along the strand of suture comprising:

a) an elongated member having a proximate end and a distal end, a peripheral surface, an axis of elongation;

b) a tip portion having a peripheral surface removably mounted to with said elongated member at said distal end, where said tip portion has an axially extending cavity extending at least in part therethrough and a distal wall comprising a distal face and a proximate face extending laterally where said proximate face defines the distal boundary of said cavity, said distal wall further having a transverse slit extending axially therethrough and communicating with said cavity, said tip portion further having a first axially extending slot communicating with said cavity and said transverse slit where said slot is so dimensioned and proportioned to permit said strand of suture to pass through said first axially extending slot and into said cavity, and where said transverse slit is so dimensioned and proportioned to permit said strand of suture to pass axially through said transverse slit when said slip-type knot is pushed by said distal wall along said strand of suture, said tip portion further having an open holding region distally and axially removed from said distal end and positioned arcuately a fixed distance circumferentially from said first axially extending slot and where said holding region is so configured and dimensioned to permit said strand of suture to be captively restrained from lateral movement within said holding region while said strand of suture advances axially through said holding region, where said open holding region comprises a second axially extending slot circumferentially displaced from said first axially extending slot and in communication with said cavity where said second axially extending slot is so configured and dimensioned to permit said strand of suture to be captively retained therein while said strand of suture passes axially therethrough, and where said holding region further comprises a circumferential slot interconnecting said first axially extending slot and said second axially extending slot and communicating with said cavity, said holding region further comprising a third axially extending slot located distally of said circumferential slot and arcuately removed a fixed distance circumferentially from said second axially extending slot, and a step slot circumferentially connecting said second axially extending slot and said third axially extending slot where said step slot communicates with said cavity.

14. The improved knot pushing instrument recited in claim 13 wherein said tip portion has an open suture channel in said peripheral surface laterally spaced from said first axially extending slot, said distal wall and extending axially in said peripheral surface.

* * * * *